US007718162B2

(12) United States Patent
Stefely et al.

(10) Patent No.: US 7,718,162 B2
(45) Date of Patent: May 18, 2010

(54) MEDICINAL AEROSOL COMPOSITIONS WITH A FUNCTIONALIZED POLYETHYLENEGLYCOL EXCIPIENT

(75) Inventors: James S. Stefely, Woodbury, MN (US); Daniel C. Duan, St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 1265 days.

(21) Appl. No.: 10/327,200

(22) Filed: Dec. 20, 2002

(65) Prior Publication Data

US 2003/0152521 A1 Aug. 14, 2003

Related U.S. Application Data

(60) Provisional application No. 60/342,787, filed on Dec. 21, 2001.

(51) Int. Cl.

| | |
|---|---|
| *A61K 9/12* | (2006.01) |
| *A61K 31/74* | (2006.01) |
| *A61K 47/48* | (2006.01) |
| *A61F 13/00* | (2006.01) |
| *C08G 63/02* | (2006.01) |

(52) U.S. Cl. ...................... 424/45; 424/78.17; 424/435; 528/272

(58) Field of Classification Search .................. 424/45, 424/78.17, 435; 528/272

See application file for complete search history.

(56) References Cited

U.S. PATENT DOCUMENTS

| | | | | | |
|---|---|---|---|---|---|
| 3,281,377 | A | * | 10/1966 | Lederer et al. | 521/134 |
| 4,863,720 | A | | 9/1989 | Burghart et al. | |
| 4,869,899 | A | | 9/1989 | Burghart et al. | |
| 5,225,183 | A | | 7/1993 | Purewal et al. | |
| 5,342,940 | A | * | 8/1994 | Ono et al. | 544/218 |
| 5,492,688 | A | | 2/1996 | Byron et al. | |
| 5,508,023 | A | | 4/1996 | Byron et al. | |
| 5,569,450 | A | | 10/1996 | Duan et al. | |
| 5,676,930 | A | | 10/1997 | Jager et al. | |
| 5,676,931 | A | | 10/1997 | Adjei et al. | |
| 5,725,841 | A | * | 3/1998 | Duan et al. | 424/45 |
| 5,770,559 | A | | 6/1998 | Manning et al. | |
| 5,846,521 | A | | 12/1998 | Somani et al. | |
| 6,042,811 | A | | 3/2000 | Duan et al. | |
| 6,126,919 | A | | 10/2000 | Stefely et al. | |
| 6,136,294 | A | | 10/2000 | Adjei et al. | |
| 6,218,353 | B1 | | 4/2001 | Romack et al. | |
| 6,258,857 | B1 | | 7/2001 | Iijima et al. | |
| 6,284,749 | B1 | | 9/2001 | Castillo et al. | |
| 2003/0138381 | A1 | | 7/2003 | Duan et al. | |
| 2003/0152521 | A1 | | 8/2003 | Stefely et al. | |

FOREIGN PATENT DOCUMENTS

| | | |
|---|---|---|
| WO | WO 94/13263 | 6/1994 |
| WO | WO 96/19197 | 6/1996 |
| WO | WO 02/03958 | 1/2002 |
| WO | WO 02/24623 | 3/2002 |
| WO | WO 02/094200 | 11/2002 |
| WO | WO 03/035237 | 5/2003 |

OTHER PUBLICATIONS

Jashnani, R.N., Dalby, R.N., Byron, P.R., "Preparation, Characterization, and Dissolution Kinetics of Two Novel Albuterol Salts", J. Pharm. Sci., 82(6), p. 613-616.

Berg, S.M., Bighley, L.D., Monkhouse, D.C., "Pharmaceutical Salts", J. Pharm. Sci., 66(1), p. 1-19.

Meakin, B.J., D.A. Lewis, D. Ganderton, and G. Brambilla (2000) "Countering Challenges Posed by Mimicry of CFC Performance Using HFA Systems", in proceedings of Respiratory Drug Delivery VII, R. Dalby, P. Byron, S. Farr, and J. Peart, editors. Serentec Press, Inc., Raleigh, NC.

Brambilla, G., D. Ganderton, R. Garzia, D. Lewis, B. Meakin, P. Ventura (1999). "Modulation of Aerosol Clouds Produced by Pressurised Inhalation Aerosols", International Journal of Phamraceutics, 186:53-61.

Stefely J, Duan D, Myrdal P, Ross D, Schultz D, and Leach C L (2000) "Design and Utility of a novel class of biocompatible excipients for HFA-based MDIs". Respiratory Drug Delivery VII, 82-90.

* cited by examiner

*Primary Examiner*—Yong S Chong

(57) ABSTRACT

The invention comprises a medicinal aerosol composition comprising a propellant, an excipient comprising a functionalized polyethyleneglycol, and a drug. The invention also comprises particulate medicinal compositions comprising particles with a mean mass aerodynamic diameter of less than about 10 microns that incorporate an excipient comprising a functionalized polyethyleneglycol.

11 Claims, No Drawings

MEDICINAL AEROSOL COMPOSITIONS WITH A FUNCTIONALIZED POLYETHYLENEGLYCOL EXCIPIENT

This application claims benefit of priority to provisional patent application 60/342,787, filed Dec. 21, 2001.

FIELD

The present invention relates to medicinal aerosol compositions and products, and in particular to excipients for use in such compositions and products.

BACKGROUND OF THE INVENTION

The delivery of a therapeutically active compound (i.e., a drug) to a living organism is generally affected by a number of parameters beyond the actual chemical identity and pharmacological activity of the drug.

Medicinal aerosols can be an effective way to introduce a drug into the pulmonary system via oral or nasal inhalation, but there are a number of important parameters governing medicinal aerosol compositions that affect their performance. The relative importance of these parameters can vary depending on the type of dosage form used (e.g., metered dose inhaler or MDI, dry powder inhaler, nebulizer) and the type of drug being delivered, but will usually include such things as the concentration of drug in the dosage form, the particle size of the aerosol that is delivered to an organism, the physicochemical stability of the composition, and the ability of particles delivered to the pulmonary system to be absorbed by the body.

In order to achieve certain desirable properties or an acceptable balance of properties it is sometimes desirable to incorporate various excipients into a medicinal aerosol composition. As used in this application, an "excipient" refers broadly to any formulation additive other than the primary active drug moiety used to improve some aspect of the formulation. Many different excipients have been suggested for use in medicinal aerosols, for such things as solubilizing drug, physically stabilizing or dispersions of drug particles, increasing the emitted particle size, and so on. But many proposed excipients, while perhaps providing one or more benefits, suffer from drawbacks that make them otherwise undesirable for use, such as toxicological problems, manufacturing difficulties, limited solubility or detrimental interactions with other product components. Hence, there is an ongoing need for new and effective excipients that are useful in medicinal aerosols, particular pressurized medicinal aerosols using hydrofluorocarbon propellants, such as HFC-134a and HFC-227. Although tremendous research investment has been made over the last decade, formulating CFC-free pressurized metered dose inhalers that are suitable in terms of the stringent functional and therapeutic requirements today continues to be of major importance.

SUMMARY OF THE INVENTION

Although the use of polyethylene glycol (PEG) as an excipient is known, it has now been found that the usefulness of polyethylene glycol can be improved if it is functionalized as set forth herein. The present invention provides a medicinal aerosol composition comprising a propellant, an excipient comprising a compound of the structure $R_1$—(O—$CH_2$—$CH_2$)$_n$—X, and a drug. X is selected from the group consisting of: —C(O)OH; —S($O_2$)OH; —OS($O_2$)OH; —P$(OH)_2$O; —OP$(OH)_2$O; —N($R_2$)($R_2$); —OC($R_2$)($R_2$)—C(O)—Z; —OC(O)—$R_2$—C(O)—Z; —O—$R_3$—C(O)—Z; and —OC(O)CH($R_3$)—N($R_2$)($R_2$). Z is selected from —OH, —N($R_2$)($R_2$); —NH—$R_2$—NH—; an amino acid residue, a peptide residue with from 2 to 8 amino acids, or a hydroxy acid. $R_1$ is methyl or ethyl. Each $R_2$ is independently selected from hydrogen or linear, branched, or cyclic hydrocarbon with 1 to 6 carbons. $R_3$ is selected from hydrogen or linear, branched, or cyclic hydrocarbon with 1 to 6 carbons, wherein $R_2$ and $R_3$ may optionally be connected together to form an alkylene bridge of from 2 to 4 carbons.

In a preferred embodiment, the compositions of the invention are solutions containing hydrofluorocarbon propellant, most preferably HFC 134a and/or HFC 227. In another preferred embodiment, the compositions of the invention are suspensions containing hydrofluorocarbon propellant.

In another aspect, the present invention provides a particulate medicinal composition comprising particles incorporating a drug and an excipient comprising a compound of the structure $R_1$—(O—$CH_2$—$CH_2$)$_n$—X, wherein the particles have a mass mean aerodynamic diameter of less than about 10 microns, preferably less than about 5 microns. X is selected from the group consisting of: —C(O)OH; —S($O_2$)OH; —OS($O_2$)OH; —P$(OH)_2$O; —OP$(OH)_2$O; —N($R_2$)($R_2$); —OC($R_2$)($R_2$)—C(O)—Z; —OC(O)—$R_2$—C(O)—Z; —O—$R_3$—C(O)—Z; and —OC(O)CH($R_3$)—N($R_2$)($R_2$). Z is selected from —OH, —N($R_2$)($R_2$); —NH—$R_2$—NH—; an amino acid residue, a peptide residue with from 2 to 8 amino acids, or a hydroxy acid. $R_1$ is methyl or ethyl. Each $R_2$ is independently selected from hydrogen or linear, branched, or cyclic hydrocarbon with 1 to 6 carbons. $R_3$ is independently selected from hydrogen or linear, branched, or cyclic hydrocarbon with 1 to 6 carbons, wherein $R_2$ and $R_3$ may optionally be connected together to form an alkylene bridge of from 2 to 4 carbons.

In a preferred embodiment of this aspect of the invention the drug and excipient form a hydrophilic ion pair complex. In another preferred embodiment of this aspect of the invention the drug and excipient form a pharmaceutical salt. In still another preferred embodiment of this aspect of the invention the drug and excipient form a waxy solid.

DETAILED DESCRIPTION OF THE INVENTION

The present invention provides a medicinal aerosol composition comprising a propellant, an excipient comprising a compound of the structure $R_1$—(O—$CH_2$—$CH_2$)$_n$—X, and a drug.

Suitable propellants include, for example, chlorofluorocarbons (CFCs), such as trichlorofluoromethane (also referred to as propellant 11), dichlorodifluoromethane also referred to as propellant 12), and 1,2-dichloro-1,1,2,2-tetrafluoroethane (also referred to as propellant 114), hydrochlorofluorocarbons (HCFCs), hydrofluorocarbons (HFCs), such as 1,1,1,2-tetrafluoroethane (also referred to as propellant 134a, HFC-134a, or HFA-134a) and 1,1,1,2,3,3,3-heptafluoropropane (also referred to as propellant 227, HFC-227, or HFA-227), carbon dioxide, dimethyl ether, or hydrocarbons such as butane and propane, or mixtures of any of the foregoing. Preferably, the propellant includes a hydrochlorofluorocarbon, a hydrofluorocarbon, or mixtures thereof. More preferably, a hydrofluorocarbon is used as the propellant. Most preferably, HFC-227 and/or HFC-134a are used as the propellant. The propellant is preferably present in an amount sufficient to propel a plurality of doses of the drug from an aerosol canister, preferably a metered dose inhaler.

Suitable excipients comprise compounds of the structure $R_1$—(O—$CH_2$—$CH_2$)$_n$—X.

X is selected from the group consisting of: —C(O)OH; —S(O$_2$)OH; —OS(O$_2$)OH; —P(OH)$_2$O; —OP(OH)$_2$O; —N(R$_2$)(R$_2$); —OC(R$_2$)(R$_2$)—C(O)—Z; —OC(O)—R$_2$—C(O)—Z; —O—R$_3$—C(O)—Z; and —OC(O)CH(R$_3$)—N(R$_2$)(R$_2$). Z is selected from —OH, —P(OH)$_2$O; —OP(OH)$_2$O; an amino acid residue, a peptide residue with from 2 to 8 amino acids, or a hydroxy acid.

In one such embodiment, Z is an amino acid residue bonded to the carbonyl terminus of the polyethyleneglycol chain. Z may also be a peptide residue bonded to the carbonyl terminus of the polyethyleneglycol chain, where the peptide comprises from 2 to 8 amino acids.

Preferred amino acid residues include α-amino acid residues and those that are derived from endogenous amino acids. Preferred α-amino acid residues include those of the formula —NH—R$_4$—C(O)OH wherein R$_4$ is straight chain, branched chain, or cyclic alkylene containing one catenary carbon atom and a total of one to about 12 carbon atoms, optionally substituted by one or more of lower alkoxy, lower alkylthio, carboxy, mercapto, hydroxy, phenyl, hydroxyphenyl, indolyl, guanidinyl, carbamido (i.e., —NHC(O)NH$_2$), imidazolyl, or acylamino (i.e., —C(O)NH$_2$).

More preferred amino acid residues are those that are derived from endogenous amino acids or esters thereof such as glycine, glycineamide, alanine, valine, leucine, isoleucine, serine, threonine, phenylalanine, tyrosine, tryptophan, cysteine, methionine, aspartic acid, glutamic acid, asparagine, glutamine, lysine, hydroxylysine, arginine, citrulline, histidine, proline, and hydroxyproline. Taurine, a β-amino sulfonic acid, and p-aminobenzoic acid are also suitable. Most preferred are glycine, alanine, proline, taurine, and sarcosine Preferred hydroxy acids include isethionic acid.

R$_1$ is methyl or ethyl. Each R$_2$ is independently selected from hydrogen or linear, branched, or cyclic hydrocarbon with 1 to 6 carbons. R$_3$ is independently selected from hydrogen or linear, branched, or cyclic hydrocarbon with 1 to 6 carbons, wherein R$_2$ and R$_3$ may optionally be connected together to form an alkylene bridge of from 2 to 4 carbons.

The number of repeat units, n, is from 1 to 250, preferably from 2 to 100, more preferably from 2 to 45, and most preferably 6 to 20.

Among the advantages of these excipients is the ability to increase the solubility of acid- or amine-containing drugs in HFA propellant systems. The ability of these excipients to increase drug solubility in metered dose inhalers without the need to add large amounts of low- or semi-volatile cosolvents can also allow for delivery of a high respirable fraction and a large respirable mass. These excipients can provide improved suspension quality in suspension medicinal formulations.

Medicinal formulations according to the present invention contain a drug either dispersed or dissolved in the formulation in a therapeutically effective amount. As used herein the term "therapeutically effective amount" means an amount sufficient to induce a therapeutic effect, such as bronchodilation or antiviral activity. The amount will vary according to factors known to those skilled in the art, such as the pharmacological activity of the particular drug, the condition being treated, the frequency of administration, the treatment site, and any other therapeutic agents being coadministered.

As used herein, the term "drug," includes its equivalents, "bioactive agent," and "medicament" and is intended to have its broadest meaning as including substances intended for use in the diagnosis, cure, mitigation, treatment or prevention of disease, or to affect the structure or function of the body. The drugs can be neutral or ionic. Preferably, they are suitable for oral and/or nasal inhalation. Delivery to the respiratory tract and/or lung, in order to effect bronchodilation and to treat conditions such as asthma and chronic obstructive pulmonary disease, is preferably by oral inhalation. Alternatively, to treat conditions such as rhinitis or allergic rhinitis, delivery is preferably by nasal inhalation.

Suitable drugs include, for example, antiallergics, analgesics, bronchodilators, antihistamines, antiviral agents, antitussives, anginal preparations, antibiotics, anti-inflammatories, immunomodulators, 5-lipoxygenase inhibitors, leukotriene antagonists, phospholipase A$_2$ inhibitors, phosphodiesterase IV inhibitors, peptides, proteins, steroids, and vaccine preparations. A group of preferred drugs include adrenaline, albuterol, atropine, beclomethasone dipropionate, budesonide, butixocort propionate, clemastine, cromolyn, epinephrine, ephedrine, fentanyl, flunisolide, fluticasone, formoterol, ipratropium bromide, isoproterenol, lidocaine, morphine, nedocromil, pentamidine isoethionate, pirbuterol, prednisolone, salmeterol, terbutaline, tetracycline, 4-amino-α,α,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and mixtures thereof. Particularly preferred drugs include beclomethasone dipropionate, butixocort propionate, pirbuterol, 4-amino-α,α,2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and mixtures thereof. Proteins and peptides are also particularly preferred drugs.

For oral and/or nasal inhalation, formulations where the drug is in solution are generally preferred; however, if suspensions are used, preferably the drug is micronized (i.e., in the form of particles having a diameter on the order of micrometers). More preferably, a therapeutically effective fraction of the drug (typically, about 90% or more) is in the form of particles having a diameter of less than about 10 micrometers, and most preferably, less than about 5 micrometers. These particle sizes also apply for the formulations of drug and amide and/or ester containing excipient used in dry powder inhalers. This helps ensure that the drug can be inhaled into the respiratory tract and/or lungs. It will be recognized that such limitations do not necessarily exist for nasal inhalation.

Preferably, medicinal formulations according to the present invention include a drug in an amount and in a form such that the drug can be administered as an aerosol. More preferably, the drug is present in an amount such that the drug can produce its desired therapeutic effect with one dose from a conventional aerosol canister with a conventional valve, such as a metered dose valve. As used herein, an "amount" of the drug can be referred to in terms of quantity or concentration. A therapeutically effective amount of a drug can vary according to a variety of factors, such as the potency of the particular drug, the route of administration of the formulation, the mode of administration of the formulation, and the mechanical system used to administer the formulation. A therapeutically effective amount of a particular drug can be selected by those of ordinary skill in the art with consideration of such factors. Generally, a therapeutically effective amount will be from about 0.02 parts to about 2 parts, more preferably from about 0.1 parts to about 1 part, by weight based on 100 parts of the medicinal formulation.

Medicinal formulations according to the present invention can include an optional cosolvent or mixtures of cosolvents. The cosolvent can be used in an amount effective to dissolve the drug and/or the excipient. Preferably, the cosolvent is used in an amount of about 0.01 to about 25% by weight, more preferably about 0.01 to about 15%, and most preferably about 0.01 to about 6%, based on the total weight of the formulation. Examples of suitable cosolvents include ethanol and isopropanol. Ethanol is a preferred cosolvent.

Other additives (i.e., excipients), such as lubricants, surfactants, and taste masking ingredients, can also be included in medicinal formulations of the present invention.

The amount of functionalized polyethyleneglycol excipient used will depend upon a number of factors, including the type and amount of drug used and the desired therapeutic effect. In a preferred embodiment the molar ratio of functionalized polyethyleneglycol excipient to drug will be between about 5:1 and 1:5, more preferably between about 2:1 and 1:2, and more preferably will be about 1:1. The excipient and drug are preferably present as a pharmaceutical salt or ion pair complex, but may also be present as a waxy mixture.

Conventional aerosol canisters, such as those of aluminum, glass, stainless steel, or polyethylene terephthalate, can be used to contain the medicinal formulations according to the present invention. Aerosol canisters equipped with conventional valves, preferably, metered dose valves, can be used to deliver the formulations of the invention. The selection of the appropriate valve assembly typically depends on the components in the medicinal formulation.

Preparation of the compositions may be by a variety of conventional methods. Where a cosolvent is used, a mixture of drug, excipient, and cosolvent may be prepared, to which propellant is subsequently added to prepare a metered dose inhaler. Alternatively, drug and excipient may be dissolved in a process solvent and recrystallized to prepare a pharmaceutical salt. The functionalized polyethyleneglycol excipients are substantially water soluble, which can be advantageous when water soluble drugs, such as proteins, are incorporated within the compositions of the present invention In another aspect, the present invention comprises a particulate medicinal composition comprising particles incorporating a drug and an excipient comprising a compound of the structure $R_1$—(O—$CH_2$—$CH_2$)$_n$—X, where X and $R_1$ are as described above, and where the particles have a mass mean aerodynamic diameter (MMAD) of less than about 10 microns, and more preferably less than about 5 microns. The mean diameter of the particles is preferably less than about 5 microns. In a preferred embodiment the drug and excipient form a pharmaceutical salt.

In one embodiment, the functionalized polyethyleneglycol is non-covalently associated with a drug in order to achieve many of the benefits of direct covalent attachment of polyethyleneglycol to drug, such as improved solubility, reduced antigenicity, and improved circulation times, without reducing activity or creating a new chemical entity.

Particulate medicinal compositions of the present invention may be used particularly within dry powder inhalers.

In another aspect, the present invention comprises an aqueous medicinal composition comprising an aqueous carrier fluid, a drug, and an excipient comprising a compound of the structure $R_1$—(O—$CH_2$—$CH_2$)$_n$—X, where X and $R_1$ are as described above. Aqueous medicinal systems include, e.g., nebulizers, pump sprays, injectables, and topical gels, creams, and lotions.

EXAMPLES

Examples 1 to 9

A drug (4-amino-2-ethoxymethyl-α,α-dimethyl-1H-imidazo[4,5-c]quinoline-1-ethanol), carboxylic acid functionalized polyethyleneglycol with a molecular weight of 350 (aPEG 350) and ethanol were added to a canister which was capped with a continuous valve. The carboxylic acid functionalized polyethyleneglycol was prepared by treating mono methylpolyethyleneglycol with t-butoxide followed by the addition of ethyl bromoacetate, and subsequent hydrolysis with HCl. HFA-134a propellant was added to the canister and mixed together to form a solution formulation. The relative weight percentages of excipient and ethanol are shown below in table 1. An excess of drug was provided. The canister was shaken for at least two days. A continuous valve was crimped onto a second, empty canister, which was chilled by being placed on dry ice. The formulation from the first canister was passed through a 0.22 micron filter, and into the second canister by depressing both continuous valves. The vapor pressure of the formulation in the first canister caused the formulation to flow through the filter. The solubility of the drug is taken as the concentration of drug in the solution that passes through the filter and into the second canister. The solution drug concentration was assayed for drug concentration using an ion exchange HPLC method with external standard quantitation and UV detection at 247 nm.

The drug solubility is shown below in table 1.

TABLE 1

| Example Number | aPEG 350 (% w/w) | Ethanol (% w/w) | Drug Solubility (% w/w) |
|---|---|---|---|
| 1 | 0.5 | 2.2 | 0.26 |
| 2 | 0.5 | 5.4 | 0.31 |
| 3 | 0.5 | 10.6 | 0.39 |
| 4 | 1.1 | 2.2 | 0.44 |
| 5 | 1.1 | 5.4 | 0.63 |
| 6 | 1.0 | 10.5 | 0.73 |
| 7 | 2.1 | 2.1 | 0.79 |
| 8 | 2.1 | 5.3 | 1.21 |
| 9 | 2.1 | 10.5 | 1.52 |

Examples 10 to 18

A series of formulations were prepared following the method of examples 1 to 9, with the exception that a carboxylic acid functionalized polyethyleneglycol with a molecular weight of 550 (aPEG 550) was used in place of carboxylic acid functionalized polyethyleneglycol with a molecular weight of 350. The relative weight percentages of each component and the drug solubility are shown below in table 2.

TABLE 2

| Example Number | aPEG 550 (% w/w) | Ethanol (% w/w) | Drug Solubility (% w/w) |
|---|---|---|---|
| 10 | 0.5 | 2.2 | 0.16 |
| 11 | 0.5 | 5.4 | 0.26 |
| 12 | 0.5 | 10.6 | 0.33 |
| 13 | 1.1 | 2.1 | 0.30 |
| 14 | 1.1 | 5.3 | 0.40 |
| 15 | 1.1 | 10.6 | 0.56 |
| 16 | 2.2 | 2.1 | 0.60 |
| 17 | 2.1 | 5.3 | 0.82 |
| 18 | 2.1 | 10.6 | 1.03 |

Examples 19 to 27

A series of formulations were prepared following the method of examples 1 to 9, with the exception that a carboxylic acid functionalized polyethyleneglycol with a molecular weight of 750 (aPEG 750) was used in place of carboxylic acid functionalized polyethyleneglycol with a molecular weight of 350. The relative weight percentages of each component and the drug solubility are shown below in table 3.

TABLE 4

| Example Number | Drug (% w/w) | aPEG350 (% w/w) | Ethanol (% w/w) | HFA-134a (% w/w) | Resp. Mass (mcg/act) | Resp. Fract. (%) |
|---|---|---|---|---|---|---|
| 28 | 0.16 | 0.5 | 2.2 | 97.1 | 80.7 | 73.8 |
| 29 | 0.26 | 0.5 | 5.4 | 93.8 | 98.8 | 60.9 |
| 30 | 0.33 | 0.5 | 10.6 | 88.5 | 86.0 | 42.2 |
| 31 | 0.30 | 1.1 | 2.1 | 96.5 | 147.5 | 68.0 |
| 32 | 0.40 | 1.1 | 5.3 | 93.2 | 150.3 | 59.4 |
| 33 | 0.56 | 1.1 | 10.6 | 87.8 | 130.6 | 41.5 |
| 34 | 0.82 | 2.1 | 5.3 | 91.8 | 240.4 | 45.9 |
| 35 | 1.03 | 2.1 | 10.6 | 86.3 | 171.8 | 30.0 |

TABLE 3

| Example Number | aPEG 750 (% w/w) | Ethanol (% w/w) | Drug Solubility (% w/w) |
|---|---|---|---|
| 19 | 0.6 | 2.2 | 0.12 |
| 20 | 0.5 | 5.3 | 0.22 |
| 21 | 0.5 | 10.6 | 0.30 |
| 22 | 1.1 | 2.1 | 0.22 |
| 23 | 1.1 | 5.3 | 0.40 |
| 24 | 1.0 | 10.6 | 0.54 |
| 25 | 2.1 | 2.1 | 0.54 |
| 26 | 2.1 | 5.3 | 0.67 |
| 27 | 2.1 | 10.6 | 0.83 |

Examples 28 to 35

A drug (4-amino-2-ethoxymethyl-α,α-dimethyl-1H-imidazo[4,5-c]quinoline-1-ethanol) carboxylic acid functionalized polyethyleneglycol with a molecular weight of 350 and ethanol were added to a canister which was capped with a continuous valve. The carboxylic acid functionalized polyethyleneglycol was prepared by treating non-functionalized monopolyethyleneglycol with t-butoxide followed by the addition of ethyl bromoacetate, and subsequent hydrolysis with HCl. HFA-134a propellant was added to the canister and mixed together to form a solution formulation. The relative weight percentages of each component are shown below in table 4. The contents of the canister were chilled and transferred to a 15 mL canister and a 50 microliter Spraymiser (trademark of 3M Co.) valve was crimped onto the canister. The canister was placed into a standard solution MDI actuator with an orifice diameter of approximately 0.30 mm.

Inertial impactor measurements were conducted using the U.S. Pharmacopeia recommended inlet (as described in USP 1995, Section 601, Aerosols, p. 1764) and an impactor with a 4.7 micron cutpoint stage. Tests were conducted by actuating the MDIs five times into the inertial impactor apparatus operating at a flowrate of 28.3 liters per minute. The drug depositing on each component of the inertial impactor apparatus were determined by rinsing the component with a solution of 1 part 10.0 M HCL: 99 parts methanol (v:v) to dissolve the drug and then determining the concentration of drug in that solution using a UV absorbance method with detection at 321 nm. The respirable mass is defined as the weight of material (in micrograms) per actuation that deposited on all components of the impactor apparatus beyond the 4.7 micron cutpoint stage. Respirable fraction is defined as the weight percentage of the drug that is respirable divided by the total amount of drug delivered from the actuator. Respirable mass and respirable fraction results are shown below in table 4.

Example 36

Micronized pirbuterol acetate (30 mg), carboxylic acid functionalized polyethyleneglycol with a molecular weight of 750 (50 mg) and ethanol (100 mg) were added to a 15 mL glass aerosol vial. A continuous valve was crimped onto the vial and the vial was pressure filled with HFA-134a propellant (10 g). The vial was sonicated for 2 minutes to initially disperse the drug and mix the formulation. The vial was shaken by hand and visually observed. No flocculation was observed 60 seconds after shaking was stopped.

Comparative Example 1

Micronized pirbuterol acetate (30 mg) and ethanol (100 mg) were added to a 15 mL glass aerosol vial. A continuous valve was crimped onto the vial and the vial was pressure filled with HFA-134a propellant (10 g). The vial was sonicated for 2 minutes to initially disperse the drug and mix the formulation. The vial was shaken by hand and visually observed. Flocculation was immediately observed after shaking was stopped.

Example 37

Micronized pirbuterol acetate (30 mg), carboxylic acid functionalized polyethyleneglycol with a molecular weight of 1100 (50 mg) and ethanol (100 mg) were added to a 15 mL glass aerosol vial. A continuous valve was crimped onto the vial and the vial was pressure filled with HFA-134a propellant (10 g). The vial was sonicated for 2 minutes to initially disperse the drug and mix the formulation. The vial was shaken by hand and visually observed. No flocculation was observed 60 seconds after shaking was stopped.

Example 38

Micronized pirbuterol acetate (30 mg), glycine functionalized polyethyleneglycol with a molecular weight of 1100 (50 mg) and ethanol (100 mg) were added to a 15 mL glass aerosol vial. The glycine functionalized peg acid was prepared by adding a 1.2 molar excess each of glycine t-butyl ester HCl, triethylamine, and the coupling agent EDC to a dichloromethane solution the acid functionalized polyethylene glycol of Example 37. The t-butyl group was removed by refluxing the reaction product in dichloromethane in the presence of an amberlyst 15 acid resin. Filtration was followed by removal of the solvent resulting in the desired glycine functionalized polyethylene glycol. A continuous valve was crimped onto the vial and the vial was pressure filled with HFA-134a propellant (10 g). The vial was sonicated for 2 minutes to initially disperse the drug and mix the formulation. The vial was shaken by hand and visually observed. No flocculation was observed 60 seconds after shaking was stopped.

Example 39

Micronized pirbuterol acetate (30 mg), carboxylic acid functionalized polyethyleneglycol with a molecular weight of 2000 (50 mg) and ethanol (100 mg) were added to a 15 mL glass aerosol vial. A continuous valve was crimped onto the vial and the vial was pressure filled with HFA-134a propellant (10 g). The vial was sonicated for 2 minutes to initially disperse the drug and mix the formulation. The vial was shaken by hand and visually observed. No flocculation was observed 60 seconds after shaking was stopped.

Example 40

Micronized beclomethasone dipropionate (40 mg), carboxylic acid functionalized polyethyleneglycol with a molecular weight of 1100 (50 mg) and ethanol (100 mg) were added to a 15 mL glass aerosol vial. A continuous valve was crimped onto the vial and the vial was pressure filled with HFA-134a propellant (10 g). The vial was sonicated for 2 minutes to initially disperse the drug and mix the formulation. The vial was shaken by hand and visually observed. No flocculation was observed 60 seconds after shaking was stopped.

Example 41

Albuterol free base (40 mg), carboxylic acid functionalized polyethyleneglycol with a molecular weight of 1100 (50 mg) and ethanol (100 mg) were added to a 15 mL glass aerosol vial. A continuous valve was crimped onto the vial and the vial was pressure filled with HFA-134a propellant (10 g). The vial was sonicated for 2 minutes to initially disperse the drug and mix the formulation. The vial was shaken by hand and visually observed. No flocculation was observed 60 seconds after shaking was stopped.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow

We claim:

1. A medicinal aerosol composition comprising:
    a propellant selected from the group consisting of 1,1,1,2-tetrafluoroethane, 1,1,1,2,3,3,3-heptafluoropropane, and a mixture thereof;
    an excipient comprising a compound of the structure $R_1$—(O—$CH_2$—$CH_2$)$_n$—X; wherein
    X is selected from the group consisting of: —C(O)OH; —S($O_2$)OH; —OS($O_2$)OH; —P(OH)$_2$O; —OP(OH)$_2$O; —N($R_2$)($R_2$); —OC($R_2$)($R_2$)—C(O)—Z; —OC(O)—$R_2$—C(O)—Z; —O—$R_3$—C(O)—Z; and —OC(O)CH($R_3$)—N($R_2$)($R_2$);
    Z is selected from —OH; —N($R_2$)($R_2$); —NH—$R_2$—NH—; an amino acid residue; a peptide residue with from 2 to 8 amino acids; or a hydroxy acid;
    n is from 1 to 250;
    $R_1$ is methyl or ethyl;
    Each $R_2$ is independently selected from hydrogen or linear, branched, or cyclic hydrocarbon with 1 to 6 carbons; and
    $R_3$ is independently selected from hydrogen or linear, branched, or cyclic hydrocarbon with 1 to 6 carbons, wherein $R_2$ and $R_3$ may optionally be connected together to form an alkylene bridge of from 2 to 4 carbons; and
    a drug.

2. The medicinal aerosol composition of claim 1 wherein X is —OC($R_2$)($R_2$)—C(O)—Z.

3. The medicinal aerosol composition of claim 2 wherein Z is —OH.

4. The medicinal aerosol composition of claim 2 wherein Z is an amino acid residue selected from the group consisting of glycine, glycineamide, alanine, proline, taurine, and sarcosine.

5. The medicinal aerosol composition of claim 1 wherein n is from 2 to 45.

6. The medicinal aerosol composition of claim 1 wherein the drug, excipient, and propellant form a solution.

7. The medicinal aerosol composition of claim 1 wherein the composition comprises a suspension in the propellant.

8. The medicinal aerosol composition of claim 1 further comprising a polar cosolvent.

9. The medicinal aerosol composition of claim 8 wherein the polar cosolvent is selected from the group consisting of ethanol, isopropanol, and mixtures thereof.

10. The medicinal aerosol composition of claim 1 wherein the molar ratio of excipient to drug is between about 5:1 and 1:5.

11. The medicinal aerosol composition of claim 1 wherein the molar ratio of excipient to drug is about 1:1.

* * * * *

UNITED STATES PATENT AND TRADEMARK OFFICE
CERTIFICATE OF CORRECTION

| | | |
|---|---|---|
| PATENT NO. | : 7,718,162 B2 | Page 1 of 1 |
| APPLICATION NO. | : 10/327200 | |
| DATED | : May 18, 2010 | |
| INVENTOR(S) | : James S Stefely | |

It is certified that error appears in the above-identified patent and that said Letters Patent is hereby corrected as shown below:

Title Page, Column 2
Under "Other Publications", line 13, delete "Phamraceutics," and insert
-- Pharmaceutics, --, therefor.

Column 3
Line 31, after "sarcosine" insert -- . --.

Column 5
Line 34, after "invention" insert -- . --.

Column 7
Line 38, delete "ethanol)" and insert -- ethanol), --, therefor.

Column 10
Line 2, after "follow" insert -- . --.
Line 20, Claim 1, delete "Each" and insert -- each --, therefor.

Signed and Sealed this
Twenty-fourth Day of May, 2011

David J. Kappos
*Director of the United States Patent and Trademark Office*